United States Patent [19]

Cohen et al.

[11] Patent Number: 5,558,914

[45] Date of Patent: Sep. 24, 1996

[54] WATER-BASED FORMULATION FOR THE TREATMENT OF SUNBURN

[75] Inventors: Peter D. Cohen, Edison; Carl Haight, Lincoln Park, both of N.J.

[73] Assignee: Water-Jel Technologies, Inc., Carlstadt, N.J.

[21] Appl. No.: 226,122

[22] Filed: Apr. 11, 1994

[51] Int. Cl.⁶ ........................................ A61K 7/42
[52] U.S. Cl. .............................. 424/59; 514/458
[58] Field of Search ............... 424/59, 195; 514/458

[56] References Cited

U.S. PATENT DOCUMENTS

| | | | |
|---|---|---|---|
| 3,322,624 | 5/1967 | Stone | 424/47 |
| 4,052,513 | 10/1977 | Kaplan | 424/310 |
| 4,344,965 | 8/1982 | Stone | 424/310 |
| 4,748,022 | 5/1988 | Busciglio | 424/195.1 |
| 4,933,362 | 6/1990 | Loomstein | 514/420 |
| 5,009,890 | 4/1991 | DiPippo | 424/195.1 |

OTHER PUBLICATIONS

Mangus et al, Burn Unit Pharm., Chico Commun. Mem. Hosp., 1977, 3/4(257–260), Embase No. 78140509.

Moiniche et al, Regional Anesthetic, 1993, V18, N5, pp. 300–303.

*Primary Examiner*—Shelley A. Dodson
*Attorney, Agent, or Firm*—Kenyon & Kenyon

[57] ABSTRACT

This invention relates to a water-based formulation for the treatment and care of sunburn and, in particular, to a water-based formulation that is useful for decreasing the temperature at the surface of a sunburn and for reducing the pain and discomfort caused by sunburn. The preferred water-based formulation includes tea tree oil, spearmint oil, lidocaine HCl and a component reduces tackiness.

24 Claims, No Drawings

WATER-BASED FORMULATION FOR THE TREATMENT OF SUNBURN

FIELD OF THE INVENTION

The subject invention relates to a water-based formulation and method for the treatment of sunburn.

BACKGROUND OF THE INVENTION

Although there has been substantial effort in recent years to reduce or eliminate the risk of sunburn (erythema) produced by certain wavelengths in the ultraviolet (UV) region of the spectrum, there are still circumstances wherein skin becomes exposed to UV radiation. Such exposure may, in some cases, cause sunburn that needs to be treated.

To be useful, a formulation that is intended for treatment of sunburn would preferably satisfy several objectives simultaneously. The main objectives of a formulation for the treatment of sunburn are to relieve pain, eliminate the source of heat, stop the burn progression and, if necessary, help prevent infection. Thus, a useful sunburn formulation preferably provides immediate relief from pain while also helping to promote healing. In addition, a useful sunburn formulation preferably contains components that provide protection from bacteria to which the formulation may be exposed during storage or after its application. It is also desirable that the separate components of the formulation be combined in a reasonably convenient and cost-effective process and that the composition, thus prepared, remains stable during storage. Finally, it is preferable that the sunburn formulation be contained in a carrier container so that the formulation may be conveniently delivered and applied when needed. In addition, it is desirable for health reasons, in some cases, to package the sunburn formulation in single-dose packaging so as to reduce the risk of contamination from one usage to the next. After application, it is also preferable that the sunburn formulation provide the relief and healing effects sought without producing an uncomfortable sticky sensation and without soiling or sticking to one's clothing. The sunburn formulation also preferably does not produce a residue that has to be subsequently washed or removed from the sensitive burned area.

Known formulations in the prior art for treating sunburn have certain disadvantages. For example, sunburn treatments that provide a spray mist or a petroleum-based composition to the sunburned area do not produce a sufficiently large heat transference effect to remove heat from the sunburned area. Furthermore, petroleum-based compositions tend to produce a residue that needs to be subsequently cleansed from the tender and sensitive area of sunburned skin. Such cleansing tends to cause still further discomfort.

ADVANTAGES AND SUMMARY OF THE INVENTION

An object of the subject invention is to provide a water-based formulation for the treatment of sunburn that simultaneously satisfies all these objectives while overcoming these and other disadvantages.

In particular, an object of the subject invention is to provide a water-based formulation that simultaneously provides immediate relief from the pain caused by sunburn while also producing a healing effect.

More specifically, an object of the subject invention is to provide a water-based formulation that contains a topical anesthetic and tea tree oil or a tea tree oil blend.

Another object of the subject invention is to include a fragrance-producing component that simultaneously helps to assist in masking the odor of tea tree oil, or a tea tree oil blend, as well as to provide improved heat transference from the sunburned area.

Another specific object of the subject invention is to prepare a water-based formulation containing a stable, bacteriostatic combination of several components that may be conveniently combined in a carrier system that may be delivered and applied when needed.

It is a specific object of the present invention to prepare a water-based composition so as to make use of the effective cooling properties of water when it is applied to a sunburned area.

A particular advantage of the present invention is that the water-based formulation may be applied to a sunburned area without producing a sticky, uncomfortable sensation, herein referred to as "tackiness" after the formulation has dried and without producing a residue that needs to be subsequently removed.

These and still other objects, benefits and advantages are realized for a water-based formulation comprising a stable and thickened aqueous composition suitable for administration as a sunburn-treatment composition to the skin, the aqueous composition containing water, tea tree oil, or a tea tree oil blend, a component that is present in an amount effective to function as a topical anesthetic, a fragrance-producing component that is present in an amount effective to mask the odor emanating from tea tree oil, or a tea tree oil blend, and a component for reducing tackiness, the component for reducing tackiness being present in an amount such as to produce a water-based formulation that is capable of being substantially non-tacky after drying on the skin.

DETAILED DESCRIPTION OF THE PREFERRED EMBODIMENTS

The methods by which the objects, features and advantages of the present invention are achieved will now be described in more detail. These particulars provide a more precise description of the invention for the purpose of enabling one of ordinary skill in the art to practice the invention, but without limiting the invention to the specific embodiments described.

The water-based formulation of the subject invention may be prepared by first adding a thickening agent or mixture of thickening agents to water using known methods. The thickening agent is added in an amount that is effective to produce the desired viscosity of a water-based formulation that is be applied to the skin. The viscosity of the water-based formulation of the subject invention is preferably in the range from 30,000 to about 85,000 cps based on a Brookfield viscometer with a spindle #4 at 6 rpm. Most preferably, the viscosity of the water-based formulation is about 45,000 to about 60,000 cps based on a Brookfield viscometer with a spindle #4 at 6 rpm. The thickening agent is preferably present in the range from about 0.25 to about 1.5 weight percent based on the final total weight of the water-based formulation after all components have been included in the aqueous composition. The weight percent of each component included in the water-based formulation disclosed herein is based on the final total weight of the water-based formulation. Most preferably, the thickening agent is present in an amount corresponding to about 0.7 weight percent. Preferably, the thickening agent is a water-soluble or water-dispersible resin, for example, a carboxylic acid copolymer or mixture of carboxylic acid copolymers. The preferred carboxylic acid copolymer is Carbopol 940®, which is available from B. F. Goodrich.

The water-based formulation of the subject invention also includes an emulsifier that helps to improve the consistency and to help give the aqueous composition flow properties that make it easier to spread the sunburn formulation more evenly over a sunburned area. The emulsifier is preferably a polymeric emulsifier that is present in an amount effective for producing an aqueous composition that may be smoothly and conveniently applied in relatively large quantities over a large area of sunburned skin. Preferably, the emulsifier is a high-molecular weight acrylic acid polymer present in an amount from about 0.05 to about 0.5 weight percent of the total weight of the water-based formulation. Most preferably, the water-based formulation contains about 0.2 weight percent emulsifier. Most preferably, the emulsifier is Pemulen TR1®, available from BF Goodrich.

The total amount and ratio of components that combine to produce thickening and emulsification may be adjusted so as to achieve the desired consistency or viscosity of the overall water-based formulation such that it may be conveniently and uniformly applied over a large sunburned area.

After the thickening agent and the emulsifier are fully dispersed or dissolved in water, a chelating agent may be added. Even though de-ionized water is preferably used in the preparation of the water-based formulation of the subject invention, there may still be a significant level of trace metal ions present that can interfere with the proper functioning of the components present in the water-based formulation. The chelating agent is understood to remove trace metal ions present in solution, so as to prevent these ions from interfering with the proper functioning of subsequent components, such as the preservatives. Preferably, about 0.025–0.25 weight percent of the chelating agent is present. Most preferably, about 0.1 weight percent of the chelating agent is present. The preferred chelating agent is a salt of EDTA (ethylenediaminetetra-acetic acid). The preferred salt is the disodium salt of EDTA. The EDTA salt may be dissolved first in water before blending with the aqueous composition containing the thickening agents and the component for reducing tackiness.

Next, a preservative may be added together with a surface-active agent or surfactant that functions as a wetting agent for dispersing the preservative in water. Known bactericides may be used as the preservative, such as diazolidinyl urea, imidazolidinyl urea and various alkyl-parabens, such as methylparaben, ethylparaben, propylparaben and butylparaben, as disclosed in U.S. Pat. No. 5,009,890, which is herein incorporated by reference. The preservative functions, in part, as a bactericide for attacking any bacteria that may be introduced into the water-based formulation either before or during preparation, as well as any bacteria encountered due to exposure of the formulation during storage or at the time of its application. The preservative is present in an amount effective for protecting the water-based formulation from such bacteria. Preferably, about 0.5 to about 5 weight percent preservative is included in the water-based formulation. Most preferably, about 1 weight percent preservative is present in the final water-based formulation. Preferably, the preservative is Germaben II®, which is available from Sutton Laboratories, Inc. Germaben II® includes about 56% propylene glycol, about 30% diazolidinyl urea, about 11% methylparaben and about 3% propylparaben. Use of these pre-mixed components is preferred since it is then possible to add the mixture to an aqueous composition without the need for heating.

A surfactant that serves as a wetting agent to facilitate dispersion or dissolution of the preservative in water may also be added together with the preservative. The wetting agent for dispersing the preservative is preferably an octoxynol, a nonoxynol or an alkylarylpolyglycol ester. The wetting agent is present in an amount that is effective for dispersing the preservative in water. The preservative, together with the preservative-dispersing wetting agent, is preferably dispersed with approximately an equal weight of water before blending with the aqueous composition containing the thickening agents and the EDTA salt. Preferably, about 0.05 to about 0.3 weight percent preservative-dispersing wetting agent is present in the final water-based formulation. Most preferably, about 0.1 weight percent preservative-dispersing wetting agent is present in the final water-based formulation. Most preferably, the wetting agent is octoxynol-9, which is known as Triton X 100®.

Next, a component that is intended to function as a topical anesthetic may be added to the thickened aqueous composition. The topical anesthetic provides relief from the pain caused by sunburn over the localized area to which the water-based formulation is applied. The topical anesthetic may be present in an amount that is recognized to be safe and effective for providing such relief. While it is contemplated that other known topical anesthetics may be used, such as benzocaine, it has been found that lidocaine HCl can be combined with the other components of the subject invention in a manner such as to provide a water-based formulation having the desired range of properties. It is also contemplated that other cooling or numbing agents, such as mentholated or camphor-based products, may be included in the composition. In the preferred embodiment of the subject invention, the topical anesthetic is present in an amount corresponding to about 0.5–4.0 weight percent of the final water-based formulation. Most preferably, about 2.5 weight percent topical anesthetic is present in the water-based formulation. If lidocaine HCl is used as the topical anesthetic, it may be added first to approximately an equal amount of water before blending with the thickened aqueous composition.

Tea tree oil may then be added to the thickened aqueous composition. Tea tree oil is a natural oil obtained from *Melaleuca alternifolia,* a tree that grows on the north coastal areas of the state of New South Wales and in southern Queensland, Australia. Principle active constituents of tea tree oil are 1-terpinen-4-ol, terpinolene, cineole, sesquiterpenes, p-cymene and pinene. Similar types of oils are obtained from allied species of Melaleuca such as *Melaleuca lineariifolia* and *Melaleuca leucadendron.*

In another embodiment of the sunburn formulation, a tea tree oil blend, such as disclosed in U.S. Pat. No. 5,009,890, may be included. The tea tree oil blend may include a mixture of terpenes and terpinols that are generally naturally occurring, but such a mixture may also include synthetically prepared terpenes and terpinols. The terpene and terpinol compounds can be obtained either as pure compounds derived from the natural oils or as mixtures of components derived from plants of *Melaleuca alternifolia, Melaleuca lineariifolia, Melaleuca leucadendron, Eucalyptus longirostris* and loosely related species. In a preferred embodiment, the tea tree oil blend includes certain distillate fractions of eucalyptus oil, which provides a product having characteristics similar to those of tea tree oil.

The tea tree oil blend may have the following major constituents in the approximate percentages designated below, as determined by gas chromatography in combination with mass spectrometry. All percentages may vary by up to about plus or minus 10 weight percent.

| | |
|---|---|
| α-p-mentha-1,5,diene | 0–35 weight percent |
| α-terpineol | 15–20 weight percent |
| terpinen-4-ol | 12–15 weight percent |
| 1,8,cineole | 7–14 weight percent |
| α-terpinene | 4 weight percent |
| p-cymeme | 3–7 weight percent |
| γ-terpinene | 3–7 weight percent |
| α-pinene | 2–6 weight percent |
| limonene | 1–5 weight percent |
| aromadendrene | about 1 weight percent |
| terpinolene | 1–3 weight percent |
| myrcene | 0–1 weight percent |
| α-phellandrene | 0–14 weight percent |

The remainder of the tea tree oil blend is made up of some or all of the following compounds, with no single compound being above about 1 weight percent of the tea tree oil blend.

| | |
|---|---|
| β-pinene | humulene |
| camphene | γ-muurolene |
| camphor | α-muurolene |
| sabinene | viridiflorene |
| myrcene | piperitone |
| 1,4,cineole | piperitol |
| hexanol | α-cadinene |
| allyl hexanoate | nerol |
| p-α-dimethylstyrene | geraniol |
| α-cubebene | 8-p-cymenol |
| α-copaene | calamenene |
| α-gurjunene | α-eudesmol |
| linalool | β-eudesmol |
| l-terpineol | australol |
| β-terpineol | traces of sesquiterpenes |
| β-elemene | caryophyllene |
| alloaromadendrene | |
| 4,10-dimethyl-7-isopropyl-bicyclo(4,4,0)-1,4-decadiene | |

Since the tea tree oil blend is not a single natural oil, the variation in composition exhibited by the natural oils may be reduced so as to produce a standardized sunburn formulation. However, some variation is still present, particularly in the minor constituents.

The physical constants of the tea tree oil blend thus prepared are generally as follows:

Refractive index at 20° C.: between about 1.4743 and 1.4813

Relative density at 20-C: between about 0.890 and 0.910

Optical rotation at 20 C: between about −14° and −24°

| | |
|---|---|
| Solubility in 85% ethanol (v/v) at 20-C. | soluble in less that about 1.5 times the volume of alcohol |
| General description | clear, colorless to pale yellow liquid, mobile at 20° C. |

Since tea tree oil is flammable, tea tree oil or the tea tree oil blend should be used in an amount corresponding to less than about 20 weight percent of the water-based formulation.

The tea tree oil, or the tea tree oil blend, is preferably combined with a fragrance-producing component. While it is contemplated that many known fragrances may be included in the water-based formulation, fragrance oils such as spearmint oil, peppermint oil, clove oil, oil of wintergreen, anise and the like are preferred. Such fragrance-producing components provide a masking effect that helps reduce the odor of tea tree oil, or of a tea tree oil blend, such as to permit higher levels of tea tree oil, or a tea tree oil blend, to be used than might otherwise be acceptable. The preferred fragrance-producing component is spearmint oil. Not only does the spearmint oil tend to mask the odor of tea tree oil, or of a tea tree oil blend, it also produces its own characteristic pleasant odor. In addition, it is believed that the preferred mixture of oils, including the tea tree oil, or a tea tree oil blend, and the spearmint oil, provides an enhanced cooling effect as compared to the cooling effect provided by the water which is in the water-based formulation.

It is further believed that the net result of combining all these components in a single, specially-formulated, water-based sunburn formulation offers a unique and synergistic combination of bactericidal and cooling properties, such as are provided by the high levels of the tea tree oil, or a tea tree oil blend, and by the bactericidal preservative, together with the soothing effect provided by the topical anesthetic. Furthermore, sunburn may be treated with the subject water-based formulation without producing the undesirable side-effects, such as tackiness, that are frequently encountered, for example, with a petroleum-based composition. And in addition, the subject water-based formulation does not produce a residue that may need to be subsequently removed from a sensitive sunburned area.

The tea tree oil, or tea tree oil blend, and spearmint oil may be pre-mixed together with an anti-oxidant and a surfactant for dispersing oils to form a pre-mixed aqueous composition that may then be added and blended with the aqueous composition containing the other disclosed components in the thickened aqueous composition. The anti-oxidant serves to help reduce the tendency for the components in the water-based formulation to become oxidized. The surfactant is added to help disperse the mixture of oils in water. Preferably, the tea tree oil is present in an amount corresponding to about 0.1 to about 5 weight percent of the final water-based formulation. Most preferably, about 0.5 weight percent tea tree oil is present. In an alternate embodiment of the invention tea tree oil is added in the form of a tea tree oil blend. If a tea tree oil blend is included in the water-based composition, it is preferably about 0.1 to about 5 weight percent of said thickened aqueous composition. Most preferably, the tea tree oil blend is about 0.5 weight percent of said thickened aqueous composition.

Preferably, the amount of the fragrance-producing component present is approximately equal to the amount of tea tree oil, or the tea tree oil blend, that is, from about 0.1 to about 5 weight percent fragrance-producing component is present. The fragrance-producing component is preferably present at a level that is effective for substantially eliminating the odor of tea tree oil.

The anti-oxidant is preferably present in an amount effective to substantially eliminate the tendency for the components in the water-based formulation to become oxidized.. The anti-oxidant is preferably present in an amount approximately equal to the amount of the oils, or about 0.1 to about 5 weight percent. Most preferably, about 0.5 weight percent anti-oxidant is present. The anti-oxidant is preferably vitamin-E acetate.

The surfactant for dispersing the oils is preferably present in an amount sufficient to keep the oils dispersed in water. That is, about 0.3 to about 15 weight percent oil-dispersing surfactant is preferably present. Most preferably, about 1.5 weight percent oil-dispersing surfactant is present. Preferably, the oil-dispersing surfactant is Tween 20®.

In the next step, a neutralizing agent may be added so as to produce an acceptable final pH in the range from 4.5–7.0. Preferably, the neutralizing agent is USP grade triethanolamine, which is available as trolamine-99. Trolamine-99 is approximately 99% triethanolamine. Preferably, about 0.5 to about 5 weight percent neutralizing agent is present. Most preferably, about 1.6 weight percent neutralizing agent is present. If trolamine-99 is used as the neutralizing agent, it is preferably dispersed in an equal amount of water before blending with the overall formulation.

Finally, the water-based formulation of the subject invention also includes a component that tends to reduce the tackiness produced by the water-based formulation after it has been applied and has dried on the skin. The component for reducing tackiness is present in an amount such as to produce a water-based formulation that is capable of being substantially non-tacky after drying on the skin. Preferably, the component for reducing tackiness is a humectant/emollient, for example, a glycerate or a glycereth ester, such as a glycereth-7 triacetate. Most preferably, the component for reducing tackiness is the glycereth-7 triacetate Pelemol® G7A, which is available from Phoenix Chemical in Somerville, N.J. Preferably, the tackiness-reducing component comprises about 1–8 weight percent of the water-based formulation. Most preferably, the tackiness-reducing component comprises about 3 weight percent of the water-based formulation.

Although the order in which the components as disclosed herein is the preferred order, it is to be understood that the components may be combined using a different order while still remaining within the scope of the subject invention.

The water-based formulation, thus produced, may contain from 75–95 weight percent de-ionized water. Preferably, the water-based formulation contains from about 85–90 weight percent de-ionized water. Most preferably, about 88% weight percent de-ionized water is present.

The water-based formulation, thus prepared, has the following composition:

| | |
|---|---|
| a thickening agent | 0.25–1.5 weight percent |
| an emulsifier | 0.05–0.5 weight percent |
| a chelating agent | 0.025–0.25 weight percent |
| a preservative | 0.5–5 weight percent |
| a preservative-dispersing wetting agent | 0.05–0.3 weight percent |
| a topical anesthetic | 0.5–4 weight percent |
| tea tree oil | 0.1–5 weight percent |
| a fragrance-producing component | 0.1–5 weight percent |
| an anti-oxidant | 0.1–5 weight percent |
| an oil-dispersing surfactant | 0.3–15 weight percent |
| a neutralizing agent | 0.5–5 weight percent |
| a tackiness-reducing component | 1–8 weight percent |
| de-ionized water | 75–95 weight percent |

The water-based formulation, thus produced, is a thickened aqueous composition that may be referred to as a gel, a water-based cream or a water-based emulsion.

Such a water-based formulation may be sealed in an appropriate carrier or container. Such a carrier or container may be a tube, a bottle, a single-dose packet or the like. The single-dose packet may be a multiple-ply structure having aluminum foil as one of the layers. Preferably, the sealed single-dose packet contains about 3 to about 10 grams of the subject water-based formulation. Most preferably, the single-dose packet contains about 6 grams of the subject water-based formulation. The tube or bottle may be collapsible so as to permit convenient application of a relatively large quantity of the thickened aqueous composition to a sunburned area. Alternatively, the container may be used to provide a spray-gel of the thickened aqueous composition to the sunburned area.

This invention will now be described in detail with respect to a specific preferred embodiment thereof, it being understood that the following example is intended to be illustrative only and that the invention is not intended to be limited to the formulation and the like recited herein.

EXAMPLE OF THE PREFERRED EMBODIMENT

Using the method of preparation disclosed herein, the most preferred embodiment of the water-based formulation for the treatment of sunburn has been found to be a water-based formulation having the following composition:

| | |
|---|---|
| Carbopol 940 ® | about 0.7 weight percent |
| Pemulen TR1 ® | about 0.2 weight percent |
| the disodium salt of EDTA | about 0.1 weight percent |
| Germaben II ® | about 1 weight percent |
| Triton X 100 ® | about 0.1 weight percent |
| lidocaine HCl | about 2.5 weight percent |
| tea tree oil | about 0.5 weight percent |
| spearmint oil | about 0.5 weight perce |
| vitamin-E acetate | about 0.5 weight percent |
| Tween 20 ® | about 1.5 weight percent |
| trolamine-99 | about 1.6 weight percent |
| Pelemol ® G7A | about 3 weight percent |
| de-ionized water | about 88 weight percent |

The preferred embodiment of the subject invention, thus disclosed, has a specific gravity of about 1.01, a viscosity of about 53,000 cps based on a Brookfield viscometer with a spindle #4 at 6 rpm and a pH of about 6.5. The preferred embodiment was substantially non-tacky after applying and drying it on skin.

What is claimed is:

1. A water-based formulation for treating sunburn comprising:
   a stable and thickened aqueous composition suitable for administration as a sunburn-treatment composition to the skin, the aqueous composition containing
   (a) water,
   (b) tea tree oil,
   (c) a component that is present in an amount effective to function as a topical anesthetic,
   (d) a fragrance-producing component that is present in an amount effective to mask the odor emanating from the tea tree oil and
   (e) a component for reducing tackiness, said component for reducing tackiness being present in an amount such as to produce a water-based formulation that is capable of being substantially non-tacky after drying on the skin.

2. The water-based formulation of claim 1 wherein said thickened aqueous composition includes a tea tree oil blend.

3. The water-based formulation of claim 1 wherein said thickened aqueous composition includes a thickening agent.

4. The water-based formulation of claim 1 wherein said thickened aqueous composition includes an emulsifier.

5. The water-based formulation of claim 1 wherein said topical anesthetic is lidocaine HCl.

6. The water-based formulation of claim 1 wherein said fragrance-producing component is spearmint oil.

7. The water-based formulation of claim 1 wherein said component for reducing tackiness is a glycerate.

8. The water-based formulation of claim 1 wherein said component for reducing tackiness is Pelemol® G7A.

9. The water-based formulation of claim 1 wherein said topical anesthetic is from about 0.5 to about 4.0 weight percent of said thickened aqueous composition.

10. The water-based formulation of claim 1 wherein said topical anesthetic is about 2.5 weight percent of said thickened aqueous composition.

11. The water-based formulation of claim 1 wherein said tea tree oil is about 0.1 to about 5 weight percent of said thickened aqueous composition.

12. The water-based formulation of claim 1 wherein said tea tree oil is about 0.5 weight percent of said thickened aqueous composition.

13. The water-based formulation of claim 2 wherein said tea tree oil blend is about 0.1 to about 5 weight percent of said thickened aqueous composition.

14. The water-based formulation of claim 2 wherein said tea tree oil blend is about 0.5 weight percent of said thickened aqueous composition.

15. The water-based formulation of claim 1 wherein said fragrance-producing component is about 0.1 to about 5 weight percent of said thickened aqueous composition.

16. The water-based formulation of claim 1 wherein said fragrance-producing component is about 0.5 weight percent of said thickened aqueous composition.

17. The water-based formulation of claim 1 wherein said component for reducing tackiness is about 1 to about 8 weight percent of said thickened aqueous composition.

18. The water-based formulation of claim 1 wherein said component for reducing tackiness is about 3 weight percent of said thickened aqueous composition.

19. A container for a water-based sunburn formulation comprising:

a sealed single-dose packet containing a stable and thickened aqueous composition suitable for administration as a sunburn-treatment composition to the skin, the aqueous composition containing
  (a) water,
  (b) tea tree oil,
  (c) a component that is present in an amount effective to function as a topical anesthetic,
  (d) a fragrance-producing component that is present in an amount effective to mask the odor emanating from the tea tree oil and
  (e) a component for reducing tackiness, said component for reducing tackiness being present in an amount such as to produce a water-based formulation that is capable of being substantially non-tacky after drying on the skin.

20. The container of claim 19 wherein said sealed single-dose packet contains about 3 to about 10 grams of said thickened aqueous composition.

21. The container of claim 19 wherein said sealed single-dose packet contains about 6 grams of said thickened aqueous composition.

22. A method of preparing a water-based formulation for treating sunburn comprising:

preparing a stable and thickened aqueous composition suitable for administration as a sunburn-treatment composition to the skin, the aqueous composition containing
  (a) water,
  (b) tea tree oil,
  (c) a component that is present in an amount effective to function as a topical anesthetic,
  (d) a fragrance-producing component that is present in an amount effective to mask the odor emanating from the tea tree oil and
  (e) a component for reducing tackiness, said component for reducing tackiness being present in an amount such as to produce a water-based formulation that is capable of being substantially non-tacky after drying on the skin and sealing said thickened aqueous composition in a single-dose packet.

23. A water-based formulation for the treatment of sunburn comprising about 0.25 to about 1.5 weight percent thickening agent, about 0.05 to about 0.5 weight percent emulsifier, about 0.025 to about 0.25 weight percent chelating agent, about 0.5 to about 5 weight percent preservative, about 0.05 to about 0.3 weight percent preservative-dispersing wetting agent, about 0.5 to about 4 weight, percent topical anesthetic, about 0.1 to about 5 weight percent tea tree oil, about 0.1 to about 5 weight percent spearmint oil, about 0.1 to about 5 weight percent anti-oxidant, about 0.3 to about 15 weight percent oil-dispersing surfactant, about 0.5 to about 5 weight percent neutralizing agent, about 1 to about 8 weight percent tackiness-reducing component and about 75 to about 95 weight percent de-ionized water.

24. A water-based formulation for the treatment of sunburn comprising about 0.7 weight percent Carbopol 940®, about 0.2 weight percent Pemulen TR1®, about 0.1 weight percent of a disodium salt of EDTA, about 1.0 weight percent Germaben II®, about 0.1 weight percent Triton X 100®, about 2.5 weight percent lidocaine HCl, about 0.5 weight percent tea tree oil, about 0.5 weight percent spearmint oil, about 0.5 weight percent vitamin-E acetate, about 1.5 weight percent Tween 20®, about 1.6 weight percent trolamine-99, about 3.0 weight percent Pelemol® G7A and about 88 weight percent de-ionized water.

* * * * *